US009216395B2

(12) United States Patent
Dieterle et al.

(10) Patent No.: US 9,216,395 B2
(45) Date of Patent: Dec. 22, 2015

(54) PROCESS FOR CHARGING A LONGITUDINAL SECTION OF A CATALYST TUBE

(71) Applicant: BASF SE, Ludwigshafen (DE)

(72) Inventors: Martin Dieterle, Jersey City, NJ (US); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 168 days.

(21) Appl. No.: 14/060,406

(22) Filed: Oct. 22, 2013

(65) Prior Publication Data

US 2014/0046093 A1   Feb. 13, 2014

Related U.S. Application Data

(62) Division of application No. 12/100,123, filed on Apr. 9, 2008, now Pat. No. 8,598,065.

(60) Provisional application No. 60/910,908, filed on Apr. 10, 2007.

(30) Foreign Application Priority Data

Apr. 10, 2007   (DE) .......................... 10 2007 017 080

(51) Int. Cl.
| | |
|---|---|
| *B01J 8/06* | (2006.01) |
| *C07C 51/25* | (2006.01) |
| *B01J 8/00* | (2006.01) |
| *B01J 19/30* | (2006.01) |
| *B01J 23/00* | (2006.01) |
| *B01J 23/28* | (2006.01) |
| *B01J 23/50* | (2006.01) |
| *B01J 23/887* | (2006.01) |
| *B01J 23/888* | (2006.01) |
| *B01J 27/198* | (2006.01) |
| *B01J 35/00* | (2006.01) |
| *B01J 35/02* | (2006.01) |
| *B01J 35/08* | (2006.01) |
| *C07C 45/35* | (2006.01) |
| *C07C 51/265* | (2006.01) |
| *B01J 37/00* | (2006.01) |

(52) U.S. Cl.
CPC *B01J 8/06* (2013.01); *B01J 8/0015* (2013.01); *B01J 8/067* (2013.01); *B01J 19/30* (2013.01); *B01J 23/002* (2013.01); *B01J 23/28* (2013.01); *B01J 23/50* (2013.01); *B01J 23/8876* (2013.01); *B01J 23/8885* (2013.01); *B01J 27/198* (2013.01); *B01J 35/0006* (2013.01); *B01J 35/023* (2013.01); *B01J 35/08* (2013.01); *C07C 45/35* (2013.01); *C07C 51/252* (2013.01); *C07C 51/265* (2013.01); *B01J 37/0009* (2013.01); *B01J 2208/00752* (2013.01); *B01J 2208/00805* (2013.01); *B01J 2219/30207* (2013.01); *B01J 2219/30215* (2013.01); *B01J 2219/30416* (2013.01); *B01J 2219/30475* (2013.01); *B01J 2523/00* (2013.01)

(58) Field of Classification Search
None
See application file for complete search history.

(56) References Cited

U.S. PATENT DOCUMENTS

| | | | |
|---|---|---|---|
| 3,119,837 | A | 1/1964 | Kingsley et al. |
| 3,147,084 | A | 9/1964 | Franzen et al. |
| 3,702,259 | A | 11/1972 | Nielsen |
| 3,799,886 | A | 3/1974 | Felice et al. |
| 3,865,555 | A | 2/1975 | Elebracht et al. |
| 3,871,445 | A | 3/1975 | Wanka et al. |
| 3,901,659 | A | 8/1975 | Joklik et al. |
| 3,956,377 | A | 5/1976 | Dolhyj et al. |
| 4,077,912 | A | 3/1978 | Dolhyj et al. |
| 4,203,906 | A | 5/1980 | Takada et al. |
| 4,256,783 | A | 3/1981 | Takada et al. |
| 4,366,093 | A | 12/1982 | Shiozaki et al. |
| 4,408,079 | A | 10/1983 | Merger et al. |
| 4,496,770 | A | 1/1985 | Duembgen et al. |
| 5,144,091 | A | 9/1992 | Martan et al. |
| 5,173,468 | A | 12/1992 | Boehning et al. |
| 5,198,581 | A | 3/1993 | Kawajiri et al. |
| 5,221,767 | A | 6/1993 | Boehning et al. |
| 5,231,226 | A | 7/1993 | Hammon et al. |
| 5,264,625 | A | 11/1993 | Hammon et al. |
| 5,668,077 | A | 9/1997 | Klopries et al. |
| 5,734,068 | A | 3/1998 | Klopries et al. |
| 5,739,391 | A | 4/1998 | Ruppel et al. |
| 5,821,390 | A | 10/1998 | Ruppel et al. |
| 6,333,011 | B1 | 12/2001 | Schliephake et al. |
| 6,657,088 | B2 | 12/2003 | Schliephake et al. |
| 6,781,017 | B2 | 8/2004 | Machhammer et al. |
| 6,867,328 | B2 | 3/2005 | Borgmeier et al. |
| 7,144,557 | B2 | 12/2006 | Yada et al. |
| 7,297,814 | B2 | 11/2007 | Yada et al. |
| 7,348,443 | B2 | 3/2008 | Proll et al. |
| 7,777,082 | B2 | 8/2010 | Petzoldt et al. |
| 2003/0006026 | A1 | 1/2003 | Matsumoto et al. |

(Continued)

FOREIGN PATENT DOCUMENTS

| | | |
|---|---|---|
| DE | 1 254 137 | 1/1962 |
| DE | 2 025 430 | 12/1971 |

(Continued)

*Primary Examiner* — Jennifer A Leung
(74) *Attorney, Agent, or Firm* — Oblon, McClelland, Maier & Neustadt, L.L.P.

(57) ABSTRACT

A process for charging a longitudinal section of a catalyst tube with a homogeneous fixed catalyst bed section whose active composition is at least one multielement oxide or comprises elemental silver on an oxidic support body and whose geometric shaped catalyst bodies and shaped inert bodies have a specific inhomogeneity of their longest dimensions.

18 Claims, No Drawings

(56) References Cited

U.S. PATENT DOCUMENTS

| | | |
|---|---|---|
| 2004/0225138 A1 | 11/2004 | McAllister et al. |
| 2004/0250868 A1 | 12/2004 | Yada et al. |
| 2004/0260103 A1 | 12/2004 | Matusz et al. |
| 2005/0263926 A1 | 12/2005 | Tazawa et al. |
| 2006/0045825 A1 | 3/2006 | Dieterle et al. |
| 2006/0065064 A1* | 3/2006 | Richard et al. ............... 73/865.5 |
| 2006/0161019 A1 | 7/2006 | DeCourcy et al. |
| 2006/0205978 A1 | 9/2006 | Yunoki et al. |
| 2008/0216915 A1 | 9/2008 | Yada et al. |
| 2008/0234522 A1 | 9/2008 | Yada et al. |

FOREIGN PATENT DOCUMENTS

| | | |
|---|---|---|
| DE | 2 201 528 | 1/1972 |
| DE | 2 159 346 | 6/1972 |
| DE | 2 106 796 | 8/1972 |
| DE | 2 310 517 | 9/1973 |
| DE | 2 231 557 | 1/1974 |
| DE | 2 351 151 | 4/1974 |
| DE | 25 26 238 A1 | 1/1976 |
| DE | 25 13 405 A1 | 10/1976 |
| DE | 28 30 765 A1 | 1/1980 |
| DE | 29 03 582 A1 | 8/1980 |
| DE | 0 092 097 A1 | 10/1983 |
| DE | 40 22 212 A1 | 1/1992 |
| DE | 0 529 853 A3 | 3/1993 |
| DE | 41 32 684 A1 | 4/1993 |
| DE | 43 11 608 A1 | 12/1994 |
| DE | 44 31 949 A1 | 3/1995 |
| DE | 100 28 582 A1 | 12/2001 |
| DE | 100 46 672 A1 | 3/2002 |
| DE | 101 31 297 A1 | 1/2003 |
| EP | 0 058 927 A1 | 9/1982 |
| EP | 0 090 744 A1 | 10/1983 |
| EP | 0 372 972 A1 | 6/1990 |
| EP | 0 383 224 A2 | 8/1990 |
| EP | 0 456 837 A1 | 11/1991 |
| EP | 0 468 290 A1 | 1/1992 |
| EP | 0 522 871 A1 | 1/1993 |
| EP | 41 32 263 A1 | 4/1993 |
| EP | 0 608 838 A2 | 8/1994 |
| EP | 0 700 714 A1 | 3/1996 |
| EP | 0 873 783 A1 | 10/1998 |
| EP | 0 979 813 A1 | 2/2000 |
| EP | 1 090 684 A1 | 4/2001 |
| EP | 1 106 598 A2 | 6/2001 |
| EP | 1 270 065 A1 | 1/2003 |
| GB | 1 291 354 | 10/1972 |
| GB | 1 346 943 | 2/1974 |
| GB | 1 464 198 | 2/1977 |
| GB | 1 550 036 | 8/1979 |
| WO | WO 89/07101 | 8/1989 |
| WO | WO 01/96270 A2 | 12/2001 |
| WO | WO 03/057653 A1 | 7/2003 |
| WO | WO 03/059857 A1 | 7/2003 |
| WO | WO 2005/113123 A1 | 12/2005 |

* cited by examiner

PROCESS FOR CHARGING A LONGITUDINAL SECTION OF A CATALYST TUBE

The present application is a Divisional application of Ser. No. 12/100,123, now U.S. Pat. No. 8,598,065, claiming priority to U.S. Provisional Application No. 60/910,908 having a filing date of Apr. 10, 2007 and German Application 10 2007 017 080.9 having a filing date of Apr. 10, 2007.

The present invention relates to a process for charging a longitudinal section of a catalyst tube with a uniform fixed catalyst bed section whose active composition is at least one multielement oxide which comprises
a) the elements Mo, Fe and Bi, or
b) the elements Mo and V, or
c) the element V and additionally P and/or Sb,
or whose active composition comprises elemental silver on an oxidic support body, and which consists of a single (preferably intrinsically homogenized) type $S^i$ or of a homogenized mixture of a plurality of mutually distinguishable types $S^i$ of geometric shaped catalyst bodies or of geometric shaped catalyst bodies and geometric shaped inert bodies, where the median of the longest dimensions $L_S^i$ of the geometric shaped bodies of one type $S^i$ has a value $D_S^i$.

It is common knowledge to perform heterogeneously catalyzed partial gas phase oxidations over the fixed catalyst bed disposed in the usually vertical tubes (the so-called catalyst tubes) of tube bundle reactors (reactors which have a bundle of catalyst tubes present in a reaction vessel).

In this document, a complete oxidation of an organic compound with molecular oxygen is understood to mean that the organic compound is converted under the reactive action of molecular oxygen such that all of the carbon present in the organic compound is converted to oxides of carbon and all of the hydrogen present in the organic compound to oxides of hydrogen. All different exothermic reactions of an organic compound under the reactive action of molecular oxygen are summarized here as partial oxidations of an organic compound.

In particular, in this document, partial oxidations shall be understood to mean those exothermic reactions of organic compounds under the reactive action of molecular oxygen in which the organic compounds to be oxidized partially, after the reaction has ended, comprise at least one oxygen atom more in chemically bound form than before the partial oxidation was performed.

The tube bundle reactors required for aforementioned heterogeneously catalyzed partial gas phase oxidations are likewise known (cf., for example, DE-A 44 31 949, EP-A 700 714).

In these reactions, the reaction gas mixture is conducted through the fixed catalyst bed disposed in the catalyst tubes of the tube bundle reactor, and the reactants are converted over the catalyst surface during the residence time of the reactants.

The reaction temperature in the catalyst tubes is controlled by, inter alia, conducting a fluid heat carrier (a heat exchange medium) around the catalyst tubes of the tube bundle which are accommodated in a vessel, in order to remove energy from the reaction system. Heat carrier and reaction gas mixture may be conducted either in cocurrent or in countercurrent over the tube bundle reactor.

In addition to the possibility of conducting the heat exchange medium in a simple manner essentially immediately longitudinally to the catalyst tubes, this longitudinal conduction can also be realized merely over the entire reaction vessel and a transverse flow can be superimposed on this longitudinal flow within the reaction vessel by virtue of an arrangement, successive along the catalyst tubes, of deflecting disks which leave free passage cross sections, so as to result in a meandering flow profile of the heat exchange medium in the longitudinal section through the tube bundle (cf., for example, DE-A 44 31 949, EP-A 700 714, DE-C 28 30 765, DE-A 22 01 528, DE-A 22 31 557 and DE-A 23 10 517).

If required, essentially spatially separate heat carriers can be conducted around the catalyst tubes along different tube sections.

The tube section over which the particular heat carrier extends typically represents a single reaction zone. A variant of such multizone tube bundle reactors used with preference is the two-zone tube bundle reactor, as described, for example, by the documents DE-C 28 30 765, DE-C 25 13 405, U.S. Pat. No. 3,147,084, DE-A 22 01 528, EP-A 383224 and DE-A 29 03 582.

Suitable heat exchange media are, for example, melts of salts such as potassium nitrate, potassium nitrite, sodium nitrite and/or sodium nitrate, low-melting metals such as sodium, mercury and alloys of different metals, ionic liquids (in which at least one of the oppositely charged ions comprises at least one carbon atom), but also conventional liquids, for example water or high-boiling organic solvents (for example mixtures of Diphyl® and dimethyl phthalate).

Typically, the catalyst tubes are manufactured from ferritic steel or from stainless steel and have a wall thickness of a few mm, for example from 1 to 3 mm. Their internal diameter is usually a few cm, for example from 10 to 50 mm, frequently from 20 to 30 mm. The tube length extends normally to a few meters (a typical catalyst tube length is in the range from 1 to 8 m, frequently from 2 to 6 m, in many cases from 2 to 4 m). Appropriately from an application point of view, the number of catalyst tubes (working tubes) accommodated in the vessel extends to at least 1000, frequently at least 3000 or 5000 and in many cases to at least 10000. Frequently, the number of catalyst tubes accommodated in the reaction vessel is from 15000 to 30000 or 40000 or 50000. Tube bundle reactors having a number of catalyst tubes above 50000 are usually the exception. Within the vessel, the catalyst tubes are normally arranged in essentially homogeneous distribution, the distribution appropriately being selected such that the distance of the central internal axes of mutually adjacent catalyst tubes (the so-called catalyst tube pitch) is from 25 to 55 mm, frequently from 35 to 45 mm (cf., for example, EP-A 468 290).

Normally, in each case at least some of the catalyst tubes (working tubes) of a tube bundle reactor, appropriately from an application point of view their entirety, are manufactured homogeneously within the scope of the manufacturing means. In other words, their internal diameter, their wall thickness and their tube length are identical within narrow tolerances (cf. WO 03/059857).

The aforementioned requirement profile also frequently applies to the filling of such homogeneously manufactured catalyst tubes with shaped catalyst bodies (cf., for example, WO 03/057653), in order to ensure an optimal and substantially disruption-free operation of the tube bundle reactor. Especially for an optimal yield and selectivity of the reactions performed in the tube bundle reactor, it is essential that preferably all working tubes of the reaction are filled, i.e. charged, in a substantially uniform manner with the fixed catalyst bed.

Working tubes are typically distinguished from thermal tubes, as described, for example, by EP-A 873 783. While the working tubes are those catalyst tubes in which the chemical reaction to be performed is performed in the actual sense, thermal tubes primarily serve the purpose of monitoring and of controlling the reaction temperature in the catalyst tubes.

For this purpose, the thermal tubes normally comprise, in addition to the fixed catalyst bed, a thermowell conducted centrally along the thermal tube and provided with a temperature sensor. In general, the number of thermal tubes in a tube bundle reactor is very much smaller than the number of working tubes. Normally, the number of thermal tubes is ≤20.

Examples of heterogeneously catalyzed partial oxidations of organic compounds include the conversion of propene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf., for example, DE-A 25 26 238, EP-A 92 097, EP-A 58 927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene or naphthalene to phthalic anhydride (cf., for example, EP-A 522 871) and the conversion of butadiene to maleic anhydride (cf., for example, DE-A 21 06 796 and DE-A 16 24 921), the conversion of n-butane to maleic anhydride (cf., for example, GB-A 1 464 198 and GB-A 1 291 354), the conversion of indanes to, for example, anthraquinone (cf., for example, DE-A 20 25 430), the conversion of ethylene to ethylene oxide or of propylene to propylene oxide (cf., for example, DE-B 12 54 137, DE-A 21 59 346, EP-A 372 972, WO 89/0710, DE-A 43 11 608), the conversion of propylene and/or acrolein to acrylonitrile (cf., for example, DE-A 23 51 151), the conversion of isobutene and/or methacrolein to methacrylonitrile (i.e. the term "partial oxidation" in this document shall also comprise partial ammoxidation, i.e. a partial oxidation in the presence of ammonia), the oxidative dehydrogenation of hydrocarbons (cf., for example, DE-A 23 51 151), the conversion of propane to acrylonitrile or to acrolein and/or acrylic acid (cf., for example, DE-A 101 31 297, EP-A 1 09 0684, EP-A 608 838, DE-A 100 46 672, EP-A 529 853, WO 01/96270 and DE-A 100 28 582), etc.

The active compositions of the catalysts to be used for the performance of exothermic heterogeneously catalyzed partial gas phase oxidations of organic compounds are generally at least one multielement oxide which comprises
a) the elements Mo, Fe and Bi, or
b) the elements Mo and V, or
c) the element V and additionally P and/or Sb,
or systems which comprise elemental silver on an oxidic support.

These active compositions are shaped to shaped bodies of a wide variety of different geometries (to so-called geometric shaped catalyst bodies), in order to establish the fixed catalyst bed in the tubes of the tube bundle reactors (to charge the catalyst tubes with the fixed catalyst bed). For example, useful such geometric shaped bodies include spheres, tablets, extrudates, rings, spirals, pyramids, cylinders, prisms, cuboids, cubes, etc.

In the simplest case, the geometric shaped body may consist only of catalytically active composition which may, if appropriate, be diluted with inert material. Such geometric shaped catalyst bodies are typically referred to as unsupported catalysts.

In the case of unsupported catalysts, the shaping can be effected, for example, by compacting catalytically active powder composition (for example a pulverulent multielement oxide active composition) to the desired catalyst geometry (for example by tableting, sintering or extruding). It is possible to add shaping assistants. Alternatively, a pulverulent precursor composition can be compacted to the desired catalyst geometry and the resulting geometric shaped body can be converted by thermal treatment (if appropriate in a molecular oxygen-comprising atmosphere) to the catalytically active shaped multielement oxide body (cf., for example, US 2005/0263926).

It will be appreciated that the shaping can also be effected by coating a geometric shaped body composed of catalytically inactive material (of inert material) with active composition (also referred to hereinafter as "shaped support body" or, for short, as "support body"). Alternatively, it is also possible to coat with precursor composition and to effect the conversion to the active catalyst by subsequent thermal treatment (if appropriate in a molecular oxygen-comprising atmosphere). The coating can be effected in the simplest manner, for example, by moistening the surface of an inert support body by means of a liquid binder and subsequently adhering pulverulent active composition or pulverulent precursor composition on the moistened surface. The catalysts obtainable in this way are referred to as coated catalysts.

Suitable inert support bodies for many heterogeneously catalyzed partial gas phase oxidations are porous or nonporous aluminum oxides, silicon oxide, thorium dioxide, zirconium oxide, silicon carbide or silicates such as magnesium silicate or aluminum silicate (for example C220 steatite from CeramTec), but also metals, for example stainless steel or aluminum (cf., for example, US 2006/0205978).

Instead of coating the inert (inert generally means that, when the reaction gas mixture is conducted through a catalyst tube charged only with inert support bodies under the reaction conditions, the conversion of the reactants is ≤5 mol %, usually ≤2 mol %) support bodies with pulverulent active composition or with pulverulent precursor composition, the support body can in many cases also be impregnated with a solution of the catalytically active substance or with a solution of a precursor substance and the solvent can subsequently be volatilized and, if appropriate, a chemical reduction and/or thermal treatment (if appropriate in an atmosphere comprising molecular oxygen) can follow. The geometric shaped catalyst bodies which result in this way are typically referred to as supported or impregnated catalysts.

The longest dimension L of such geometric shaped catalyst bodies (as is quite generally the case for geometric shaped bodies in this document) is understood to mean the longest possible direct line connecting two points on the surface of the shaped catalyst body. It is (in geometric shaped inert bodies too) usually from 1 to 20 mm, often from 2 to 15 mm and in many cases from 3 or 4 to 10 or to 8 or to 6 mm. In the case of rings, the wall thickness is additionally typically from 0.5 to 6 mm, frequently from 1 to 4 or to 3 or to 2 mm.

The fixed catalyst bed does not consist of a bed of a single type of geometric shaped catalyst bodies which is uniform along the individual catalyst tube in all heterogeneously catalyzed partial gas phase oxidations over the fixed catalyst bed present in the tubes of tube bundle reactors. Instead, the fixed catalyst bed may also consist of a homogenized mixture of a plurality of (i.e. at least two) mutually distinguishable types $S^i$ of geometric shaped catalyst bodies or of geometric shaped catalyst bodies and geometric shaped inert bodies over the total length of the catalyst tube (i.e. such a mixture may consist of at least two mutually distinguishable types of geometric shaped catalyst bodies, or of a single type of geometric shaped catalyst bodies and of a single type of geometric shaped inert bodies, or at least two types of mutually distinguishable geometric shaped catalyst bodies and of a single type of geometric shaped inert bodies, or of at least two types of mutually distinguishable geometric shaped catalyst bodies and at least two types of mutually distinguishable geometric shaped inert bodies). Possible distinguishing features of the mutually different types $S^i$ are the type of geometry, the type of active composition, the type of support material, etc. Useful materials for the geometric shaped inert bodies include the same materials as have already been recommended for the inert geometric shaped support bodies in the coated catalysts and essentially do not intervene in the course of the gas phase partial oxidation. In principle, all inert shaped support bodies are also useful as geometric shaped inert bodies for diluting geometric shaped catalyst bodies in a fixed catalyst bed. Such a dilution allows the volume-specific activity of a fixed catalyst bed to be adjusted specifically to the requirement of the particular heterogeneously catalyzed partial gas phase oxidation.

The wording "homogenized mixture" means that measures have been taken in order to mix the mutually different types of geometric shaped bodies (or the different longest dimensions within one type) homogeneously with one another. Ideally, the homogeneous mixing along the entire longitudinal section achieves the statistical average, also with regard to the particular individual type.

In many cases, a catalyst tube charge (a catalyst tube filling) with a fixed catalyst bed, though, also consists of a plurality of mutually distinguishable longitudinal sections ((longitudinal) fixed catalyst bed sections, catalyst bed sections) which are mounted one on top of another (in succession). Each individual longitudinal section can be configured homogeneously over its length as has already been explained for a catalyst tube charged uniformly over its total catalyst tube length. At the transition from an intrinsically homogeneous bed section to the next intrinsically homogeneous bed section, the configuration (composition) of the bed changes abruptly. Thus, fixed catalyst beds which have a heterogeneous structure form along an individual catalyst tube. This is also referred to as a structured filling (or bed) of the catalyst tubes. At the start (viewed in flow direction of the reaction gas flowing through the catalyst tube) and/or at the end of the catalyst tube, the fixed catalyst bed is frequently concluded by an exclusive bed of geometric shaped inert bodies.

Examples of such structured fillings of catalyst tubes are described, inter alia, in the documents US 2006/0161019, EP-A 979 813, EP-A 090 744, EP-A 456 837, EP-A 1 106 598, U.S. Pat. No. 5,198,581 and U.S. Pat. No. 4,203,903.

In general, the filling of a catalyst tube with a structured fixed catalyst bed is configured such that the volume-specific activity of the fixed catalyst bed increases in flow direction of the fixed catalyst bed. The volume-specific activity of an intrinsically homogeneous longitudinal section of a fixed catalyst bed charge of a catalyst tube is increased when, with continuing charge of the catalyst tube as in the corresponding longitudinal section of the catalyst tube under otherwise identical reaction conditions (i.e. identical composition of the reactions gas mixture, identical loading of the fixed catalyst bed charge with reaction gas mixture and identical entrance temperature of the heat carrier and identical flow conditions of the heat carrier), an increased reactant conversion results (based on single pass of the reaction gas mixture through the catalyst tube).

The loading of a fixed catalyst bed catalyzing a reaction step with reaction gas or with a reaction gas component is understood to mean the amount of reaction gas or of reaction gas component in standard liters (=l (STP); the volume in liters that the corresponding amount of reaction gas or reaction gas component would take up under standard conditions, i.e. at 25° C. and 1 bar) which is conducted through one liter of fixed catalyst bed per hour. Pure inert material bed sections are not included.

According to the teaching of the prior art, the geometric dimensions of one type of geometric shaped catalyst bodies or of one type of geometric shaped inert bodies which are used to charge a longitudinal section of a catalyst tube with a homogeneous fixed catalyst bed for a heterogeneously catalyzed partial gas phase oxidation of an organic compound should be substantially uniform within the particular type (cf. US 2006/0205978 and WO 2005/113123).

However, in-house investigations have shown that a defined inhomogeneity of the aforementioned dimensions has an advantageous effect on the selectivity of the target product formation.

Accordingly, the present invention provides a process for charging a longitudinal section of a catalyst tube with a uniform fixed catalyst bed section whose active composition is at least one multielement oxide which comprises
a) the elements Mo, Fe and Bi, or
b) the elements Mo and V, or
c) the element V and additionally P and/or Sb,
or whose active composition comprises elemental silver on an oxidic support body, and which consists of a single (preferably intrinsically homogenized, i.e. essentially randomly distributed) type $S^i$ or of a homogenized mixture of a plurality of mutually distinguishable types $S^i$ of geometric shaped catalyst bodies or of geometric shaped catalyst bodies and geometric shaped inert bodies, where the median of the longest dimensions $L_S^i$ of the geometric shaped bodies of one type $S^i$ has a value $D_S^i$, wherein, at least within one type $S^i$ of geometric shaped bodies, the proviso M that from 40 to 70% of the total number of geometric shaped bodies belonging to $S^i$ has a longest dimension $L_S^i$ for which $$0.98 \cdot D_S^i \leq L_S^i \leq 1.02 \cdot D_S^i,$$

at least 10% of the total number of the geometric shaped bodies belonging to $S^i$ has a longest dimension $L_S^i$ for which $$0.94 \cdot D_S^i \leq L_S^i < 0.98 \cdot D_S^i,$$

at least 10% of the total number of the geometric shaped bodies belonging to $S^i$ has a longest dimension $L_S^i$ for which $$1.02 \cdot D_S^i < L_S^i \leq 1.10 \cdot D_S^i,$$

less than 5% of the total number of geometric shaped bodies belonging to $S^i$ has a longest dimension $L_S^i$ for which $$0.94 \cdot D_S^i > L_S^i, \text{ and}$$

less than 5% of the total number of the geometric shaped bodies belonging to $S^i$ has a longest dimension $L_S^i$ for which $$1.10 \cdot D_S^i < L_S^i$$

is satisfied.

Preferably in accordance with the invention, less than 3% of the total number of the geometric shaped bodies belonging to $S^i$ has a longest dimension $L_S^i$ for which $0.94 \cdot D_S^i > L_S^i$.

Moreover, preferably in accordance with the invention, less than 3% of the total number of the geometric shaped bodies belonging to $S^i$ has a longest dimension $L_S^i$ for which $1.10 \cdot D_S^i > L_S^i$.

Very particularly preferably in accordance with the invention, less than 1% of the total number of the geometric shaped bodies belonging to $S^i$ has a longest dimension $L_S^i$ for which $0.94 \cdot D_S^i > L_S^i$.

Moreover, very particularly preferably in accordance with the invention, less than 1% of the total number of the geometric shaped bodies belonging to $S^i$ has a longest dimension $L_S^i$ for which $1.10 \cdot D_S^i > L_S^i$.

Advantageously, the aforementioned conditions (provisos) are satisfied for the majority and particularly advantageously for each of the different types $S^i$ within the fixed catalyst bed section.

Particularly advantageously, in the process according to the invention, at least within one type $S^i$ of geometric shaped bodies of the fixed catalyst bed section, the proviso M* that from 50 to 60% (preferably 55%) of the total number of geometric shaped bodies belonging to $S^i$ has a longest dimension $L_S^i$ for which $$0.98 \cdot D_S^i \leq L_S^i \leq 1.02 \cdot D_S^i,$$

at least 15% of the total number of the geometric shaped bodies belonging to $S^i$ has a longest dimension $L_S^i$ for which $$0.94 \cdot D_S^i \leq L_S^i < 0.98 \cdot D_S^i,$$

at least 15% of the total number of the geometric shaped bodies belonging to $S^i$ has a longest dimension $L_S^i$ for which $$1.02 \cdot D_S^i < L_S^i \leq 1.10 \cdot D_S^i,$$

less than 5% of the total number of geometric shaped bodies belonging to $S^i$ has a longest dimension $L_S^i$ for which $$0.94 \cdot D_S^i > L_S^i, \text{ and}$$

less than 5% of the total number of the geometric shaped bodies belonging to $S^i$ has a longest dimension $L_S^i$ for which $$1.10 \cdot D_S^i < L_S^i$$

is satisfied.

Preferably in accordance with the invention, within the aforementioned framework, less than 3% of the total number of the geometric shaped bodies belonging to $S^i$ has a longest dimension $L_S^i$ for which $0.94 \cdot D_S^i > L_S^i$.

Moreover, within the aforementioned framework, advantageously less than 3% of the total number of the geometric shaped bodies belonging to $S^i$ has a longest dimension $L_S^i$ for which $1.10 \cdot D_S^i > L_S^i$.

Most preferably in accordance with the invention, within the aforementioned framework, less than 1% of the total number of the geometric shaped bodies belonging to $S^i$ has a longest dimension $L_S^i$ for which $0.94 \cdot D_S^i > L_S^i$.

Moreover, within the aforementioned framework, preferably less than 1% of the total number of the geometric shaped bodies belonging to $S^i$ has a longest dimension $L_S^i$ for which $1.10 \cdot D_S^i > L_S^i$.

Advantageously, the aforementioned framework conditions (provisos) are satisfied for the majority and particularly advantageously for each of the different types $S^i$ within the fixed catalyst bed section.

Very particularly advantageously, in the process according to the invention, at least within one type $S^i$ of geometric shaped bodies of the fixed catalyst bed section, the proviso M** that from 50 to 60% (preferably 55%) of the total number of geometric shaped bodies belonging to $S^i$ has a longest dimension $L_S^i$ for which $$0.98 \cdot D_S^i \leq L_S^i \leq 1.02 \cdot D_S^i,$$

at least 20% of the total number of the geometric shaped bodies belonging to $S^i$ has a longest dimension $L_S^i$ for which $$0.94 \cdot D_S^i \leq L_S^i < 0.98 \cdot D_S^i,$$

at least 20% of the total number of the geometric shaped bodies belonging to $S^i$ has a longest dimension $L_S^i$ for which $$1.02 \cdot D_S^i < L_S^i \leq 1.10 \cdot D_S^i,$$

less than 5% of the total number of geometric shaped bodies belonging to $S^i$ has a longest dimension $L_S^i$ for which $$0.94 \cdot D_S^i > L_S^i, \text{ and}$$

less than 5% of the total number of the geometric shaped bodies belonging to $S^i$ has a longest dimension $L_S^i$ for which $$1.10 \cdot D_S^i < L_S^i$$

is satisfied.

Preferably in accordance with the invention, within the aforementioned framework, less than 3% of the total number of the geometric shaped bodies belonging to $S^i$ has a longest dimension $L_S^i$ for which $0.94 \cdot D_S^i > L_S^i$.

Moreover, within the aforementioned framework, advantageously, less than 3% of the total number of the geometric shaped bodies belonging to $S^i$ has a longest dimension $L_S^i$ for which $1.10 \cdot D_S^i > L_S^i$.

Most preferably in accordance with the invention, within the aforementioned framework, less than 1% of the total number of the geometric shaped bodies belonging to $S^i$ has a longest dimension $L_S^i$ for which $0.94 \cdot D_S^i > L_S^i$.

Moreover, within the aforementioned framework, preferably less than 1% of the total number of the geometric shaped bodies belonging to $S^i$ has a longest dimension $L_S^i$ for which $1.10 \cdot D_S^i > L_S^i$.

Advantageously, the aforementioned framework conditions (provisos) are each satisfied for the majority and particularly advantageously for each of the different types $S^i$ within the fixed catalyst bed section.

Moreover, for all frameworks detailed in this document, it is particularly advantageous when no geometric shaped bodies belonging to $S^i$ have a longest dimension $L_S^i$ for which $0.94 \cdot D_S^i > L_S^i$.

Moreover, for all frameworks detailed in this document, it is particularly advantageous when no geometric shaped bodies belonging to $S^i$ have a longest dimension $L_S^i$ for which $1.10 \cdot D_S^i > L_S^i$.

The median $D_S^i$ of the longest dimensions $L_S^i$ of the geometric shaped bodies of one type $S^i$ is defined such that 50% of all (of the) longest dimensions $L_S^i$ of the geometric shaped bodies of one type $S^i$ are less than or equal to $D_S^i$ (where the median, unless explicitly stated otherwise in this document, is always formed using the particular shaped bodies present in a homogeneously charged longitudinal section of the catalyst tube).

In principle, a uniformly charged longitudinal section of the catalyst tube in the process according to the invention can extend over the entire catalyst tube length.

It will be appreciated that the entire fixed catalyst bed present in the catalyst tube may also consist of a plurality of mutually distinguishable (each intrinsically homogeneously charged) fixed catalyst bed sections (longitudinal sections). In this case, it is advantageous when the process according to the invention is applied to the majority, and particularly advantageous when it is applied to each of the different fixed catalyst bed sections.

When the fixed catalyst bed in a catalyst tube also has longitudinal sections which consist exclusively of geometric shaped inert bodies, it is advantageous when the inventive procedure is also applied to those inert sections (these too satisfy the inventive provisos). However, the application of the inventive procedure to such inert sections is less relevant than in the case of catalytically active sections (in each case, these comprise catalytically active geometric shaped catalyst bodies).

Inert sections may be used, for example, within a catalyst tube to separate catalytically active sections spatially from one another.

In the simplest case, which is preferred from an application point of view, mutually different, but in each case intrinsically homogeneous, fixed catalyst bed (longitudinal) sections (especially the catalytically active sections) of a catalyst tube may differ (at least in as far as they catalyze the same reaction step) only by virtue of a single type of geometric shaped catalyst bodies comprising active composition being diluted with a different proportion of a single type of inert geometric shaped inert bodies not comprising any active composition (in the simplest case, these may, as already stated, be inert (shaped) support bodies; but they may also be shaped inert bodies consisting of metal (for example stainless steel)) (in homogenized form). Advantageously, all fixed catalyst bed (longitudinal) sections of a catalyst tube charged with a fixed catalyst bed for a heterogeneously catalyzed partial gas phase oxidation differ exclusively in the aforementioned manner (in this case, the fixed catalyst bed longitudinal section charged only with the one type of geometric shaped catalyst bodies and the fixed catalyst bed longitudinal section charged only with the one type of geometric shaped inert bodies form the two possible dilution boundary cases). Pure inert beds may also consist of a separate type of shaped inert bodies.

In principle, within the context of the statements above, the one type of inert shaped diluent bodies (shaped inert bodies) may have either the same geometry as (which is preferred) or a different geometry from the one type of catalytically active shaped catalyst bodies.

When a single inventive fixed catalyst bed section consists of a (homogenized) mixture of only one type of geometric shaped catalyst bodies and only one type of geometric shaped inert bodies, it is advantageous in accordance with the invention (especially in the case of the same geometries of the two shaped body types) when the median $D_{cat}$ of the longest dimensions of the only one type of geometric shaped catalyst bodies and the median $D_{inert}$ of the only one type of geometric shaped inert bodies (formed over the fixed catalyst bed section) are of similar size. It is advantageous from an application point of view when $0.90 \leq D_{cat}/D_{inert} \leq 1.10$. Very particularly advantageously from an application point of view, for the ratio of the two medians, $0.95 \leq D_{cat}/D_{inert} \leq 1.05$. It is best when $0.98 \leq D_{cat}/D_{inert} \leq 1.02$, or $D_{cat}/D_{inert}=1$. The $D_{cat}/D_{inert}$ ratio shall hereinafter be abbreviated to V.

When all catalytically active fixed catalyst bed (longitudinal) sections of a fixed catalyst bed charge of a catalyst tube consist of different (homogenized) degrees of dilution (mixtures) of a single type of geometric shaped catalyst bodies with a single type of geometric shaped inert bodies (at least in as far as they catalyze the same reaction step), the aforementioned ratios are, appropriately from an application point of view, intrinsically satisfied in each individual catalytically active fixed catalyst bed (longitudinal) section having such a dilution (the two shaped body types preferably have the same geometry).

Very particularly appropriately from an application point of view (especially when the two shaped body types have the same geometry), the median ratio is within one of the aforementioned ranges when the median is formed over the entire catalytically active fixed catalyst bed disposed within the catalyst tube (or over all fixed catalyst bed (longitudinal) sections which catalyze the same reaction step) (even better, the median ratio is within one of the aforementioned ranges when pure inert beds are also included in the median formation over the entire fixed bed present in the catalyst tube).

A series arrangement of such fixed catalyst bed (longitudinal) sections having a different degree of dilution (formed from only one type of geometric shaped inert bodies and only one type of geometric shaped catalyst bodies) can generate, in each case adapted specifically to the requirements of the heterogeneously catalyzed partial gas phase oxidation to be performed, along a catalyst tube, dilution profiles (dilution structures) of a wide variety of different types, the two shaped body types, advantageously from an application point of view, having the same geometry. In many cases, the dilution structure is selected such that the degree of dilution decreases in flow direction of the reaction gas mixture (i.e. the volume-specific active composition increases in flow direction; wherever the reactant concentration is high, the volume-specific activity is low and vice versa). If required, the dilution profile (the activity structuring) can, though, be selected conversely or completely differently.

As already mentioned, preferably all catalytically active (in each case, they comprise geometric shaped catalyst bodies) fixed catalyst bed (longitudinal) sections of a fixed catalyst bed charge of a catalyst tube (at least in as far as they catalyze the same reaction step) consist of different (homogenized) degrees of dilution (mixtures) of a single type of geometric shaped catalyst bodies with a single type of geometric shaped inert bodies (including the "0" degree of dilution; such a catalytically active fixed catalyst bed (longitudinal) section consists exclusively of the one type of geometric shaped catalyst bodies).

When the one type of geometric shaped catalyst bodies and the one type of geometric shaped inert bodies advantageously, in addition, have the same geometry and a combined median $D^{inert}_{cat}$ is formed over all (over the total number G of) longest dimensions $L_{cat}$ and $L_{inert}$ of the geometric shaped catalyst bodies and of the geometric shaped inert bodies which are present in the entirety of these fixed catalyst bed (longitudinal) sections, it is advantageous in accordance with the invention when the proviso $M^G$ that from 40 to 70 (preferably from 50 to 60) % of the total number G of geometric shaped catalyst bodies and geometric shaped inert bodies has a longest dimension $L_{cat,inert}$ for which $$0.98 \cdot D^{inert}_{cat} \leq L_{cat,inert} \leq 1.02 \cdot D^{inert}_{cat},$$

at least 10 (preferably 15 or 20) % of the total number G has a longest dimension $L_{cat,inert}$ for which $$0.94 \cdot D^{inert}_{cat} \leq L_{cat,inert} < 0.98 \cdot D^{inert}_{cat},$$

at least 10 (preferably 15 or 20) % of the total number G has a longest dimension $L_{cat,inert}$ for which $$1.02 \cdot D^{inert}_{cat} < L_{cat,inert} \leq 1.10 \cdot D^{inert}_{cat},$$

less than 5 (preferably less than 3 or 1 (or 0%))% of the total number G has a longest dimension $L_{cat,inert}$ for which $$0.94 \cdot D^{inert}_{cat} > L_{cat,inert}, \text{ and}$$

less than 5 (preferably less than 3 or 1 (or 0%))% of the total number G has a longest dimension $L_{cat,inert}$ for which $$1.10 \cdot D^{inert}_{cat} < L_{cat,inert},$$

is satisfied.

However, it is also already advantageous when the proviso $M^G$ is satisfied only within a homogeneous fixed catalyst bed (longitudinal) section or at least formed over the majority of the fixed catalyst bed (longitudinal) sections.

Normally, within a catalyst tube, those fixed catalyst bed (longitudinal) sections which catalyze the same reaction step follow one another in succession in flow direction of the fixed catalyst bed.

When, within a catalyst tube, more (in the majority of cases, only one reaction step is catalyzed within a catalyst tube) than one reaction step is catalyzed (for examples first the step from propylene to acrolein and, downstream thereof in flow direction, the step from acrolein to acrylic acid), the fixed catalyst bed generally has a number of aforementioned fixed catalyst bed (longitudinal) section sequences corresponding to the number of reaction steps. When such a fixed catalyst bed (longitudinal) section sequence begins or ends with a fixed bed section consisting only of shaped inert bodies, it is favorable in accordance with the invention when these shaped inert bodies are of the same type as those used in the downstream or upstream fixed catalyst bed (longitudinal) section sequence. Moreover, it is advantageous in accordance with the invention when the aforementioned relationship framework (the aforementioned provisos $M^G$) is also satisfied when such fixed bed sections consisting only of shaped inert bodies are included.

For the production of one type $S^i$ of geometric shaped coated catalyst bodies (shaped supported catalyst bodies) which satisfy the inventive requirement profile, the starting point will generally be one type of geometric shaped support bodies which (viewed as one type of geometric shaped inert bodies) already as such satisfy the inventive requirement profile, and these will be coated (or impregnated) uniformly with finely divided active composition or with finely divided precursor composition of the active composition by known prior art processes. For this purpose, for example, the coating process described in US 2006/0205978 can be employed. Alternatively, the coating process of EP-A 714 700 can be employed.

In order to obtain one type of geometric shaped support bodies which, with regard to their longest dimensions, satisfy the inventive requirement profile, it is possible in a simple manner to proceed from geometric shaped support body types for which, between the median of their longest dimensions $D_S^*$ and the accompanying longest dimensions $L_S^*$, the relationship B $$0.99 \cdot D_S^* \leq L_S^* \leq 1.01 \cdot D_S^* \quad (B)$$

is satisfied.

Shaped support body types which are different from one another in the manner required may then be mixed homogeneously with one another (homogenized) in the required quantitative ratios. In a corresponding manner, types $S^i$ of geometric shaped inert bodies suitable in accordance with the invention are obtainable.

For the production of one type $S^i$ of geometric shaped unsupported catalyst bodies which satisfies the inventive requirement profile, it is possible to proceed in a corresponding manner. In other words, for example according to the procedure disclosed in US 2005/0263926, shaped unsupported catalyst body types (or shaped unsupported catalyst precursor body types which are yet to be calcined (to be treated thermally)) which satisfy the relationship B are obtained. Appropriate (homogenizing) blending of such mutually different types subsequently allows, in accordance with the invention, required types $S^i$ to be obtained.

Everything stated in this document applies especially when both the geometric shaped catalyst body types and the geometric shaped inert body types are rings (or spheres).

This is especially true when the active composition of such catalyst rings is a multielement oxide of the general formula I $$Mo_{12}Bi_aFe_bX^1_cX^2_dX^3_eX^4_fO_n \quad (I)$$

where
 $X^1$=nickel and/or cobalt,
 $X^2$=thallium, an alkali metal and/or an alkaline earth metal,
 $X^3$=zinc, phosphorus, arsenic, boron, antimony, tin, cerium, lead, vanadium, chromium and/or tungsten,
 $X^4$=silicon, aluminum, titanium and/or zirconium,
 a=0.2 to 5,
 b=0.01 to 5,
 c=0 to 10,
 d=0 to 2,
 e=0 to 8,
 f=0 to 10, and
 n=a number which is determined by the valency and frequency of the elements in I other than oxygen
(it will be appreciated that aforementioned multielement oxides I may also be used as the active composition for all other possible geometric shaped catalyst body types.)

Descriptions of the preparation of corresponding unsupported catalyst rings and coated catalyst rings (or spheres in each case) can be found, for example, in WO 02/30569, in WO 2005/030393, in Research Disclosure RD 2005-497012, in DE-A 10 2007 005 602 and in DE-A 10 2007 004 961. In the aforementioned documents, those annular catalysts (and quite generally catalysts with a multielement oxide I as the active composition) whose active composition is a multielement oxide I are recommended, especially for a heterogeneously catalyzed partial oxidation of propylene to acrolein or acrolein and acrylic acid, and also of isobutene to methacrolein. The ring geometries recommended in the aforementioned documents should be understood, in the context of the present invention, as median ring geometry of one type of annular shaped catalyst bodies. In other words, the median of the internal ring diameter, the median of the external ring diameter and the median of the ring length of an annular shaped catalyst body type $S^i$ to be used in accordance with the invention may have the magnitudes specified in each case in the aforementioned documents.

The external diameter of these median ring geometries may be, for example, from 2 to 10 mm, or from 2 to 8 mm, or from 4 to 8 mm (the same applies in the case of sphere geometries).

The length of these median ring geometries may likewise be, for example, from 2 to 10 mm, or from 2 to 8 mm, or from 4 to 8 mm. The median of the wall thickness of such ring geometries is appropriately generally from 1 to 3 mm.

The median of the particular ring dimension (this is also true in the case of all other ring geometries addressed in this document or other ring geometries (for example sphere geometry) of one type $S^i$ of shaped catalyst bodies in relation to the median of a specific dimension of the particular geometry and the individual values of this dimension from which its median is formed) may be in the same ratio relative to the corresponding individual values of this dimension from which it is formed as $L_S^i$ to $D_S^i$ according to the present invention.

When reference is made in this document to the same geometries of different types of geometric shaped bodies, what is meant is that the different types of geometric shaped bodies have essentially the same median geometry. In other words, the medians of mutually corresponding individual dimensions of the shaped body geometries differ, based on the arithmetic mean of the two medians, by less than 10%, preferably by less than 5%. The individual dimensions of a median geometry may in principle have the values recommended in the prior art for the corresponding dimension of an individual geometry.

A particularly preferred median ring geometry for multimetal oxide (I) shaped unsupported catalyst bodies is, for example, the geometry external diameter E 5 mm×length L 3 mm×internal diameter I 2 mm (which is already recommended as a preferred individual geometry in the prior art).

Other favorable multimetal oxide (I) unsupported catalyst median ring geometries E×L×I are the geometries 5 mm×2 mm×2 mm, or 5 mm×3 mm×3 mm, or 5.5 mm×3 mm×3.5 mm, or 6 mm×3 mm×4 mm, or 6.5 mm×3 mm×4.5 mm, or 7 mm×3 mm×5 mm, or 7 mm×7 mm×3 mm, or 7 mm×7 mm×4 mm.

All of these multimetal oxide (I) unsupported catalyst median ring geometries are suitable, for example, both for the catalytic partial oxidation of propylene to acrolein in the gas phase and for the catalytic partial oxidation of isobutene or tert-butanol or the methyl ether of tert-butanol to methacrolein in the gas phase.

Regarding the active compositions of the stoichiometry of the general formula I, the stoichiometric coefficient b is preferably from 2 to 4, the stoichiometric coefficient c preferably from 3 to 10, the stoichiometric coefficient d preferably from 0.02 to 2, the stoichiometric coefficient e preferably from 0 to 5 and the stoichiometric coefficient f advantageously from 0.5 or 1 to 10. More preferably, the aforementioned stoichiometric coefficients are simultaneously within the preferred ranges mentioned.

Moreover, $X^1$ is preferably cobalt, $X^2$ is preferably K, Cs and/or Sr, more preferably K, $X^3$ is preferably tungsten, zinc and/or phosphorus and $X^4$ is preferably Si. More preferably, the variables $X^1$ to $X^4$ simultaneously have the aforementioned definitions.

The statements made regarding the median geometries of the shaped catalyst bodies apply correspondingly to the shaped inert bodies. The shaped inert bodies are preferably manufactured from C 220 steatite from CeramTec.

Annular (spherical) shaped catalyst bodies are, appropriately from an application point of view, diluted with annular (spherical) shaped inert bodies in order to bring about an activity structuring of the catalyst charge in the catalyst tube. The annular shaped inert bodies preferably have the same median ring geometry as the annular shaped catalyst bodies (this statement also applies in the case of sphere geometry).

For a heterogeneously catalyzed partial gas phase oxidation to prepare acrolein or methacrolein, the catalyst charge in the catalyst tube with the above-described annular shaped bodies is preferably either configured uniformly with only one inventive type $S^i$ of unsupported catalyst rings for the entire length of the catalyst tube or structured as follows.

Positioned at the catalyst tube inlet (in flow direction of the reaction gas mixture), for a length of from 10 to 60%, preferably from 10 to 50%, more preferably from 20 to 40% and most preferably from 25 to 35% (i.e., for example, for a length of from 0.70 to 1.50 m, preferably from 0.90 to 1.20 m), in each case of the total length of the catalytically active catalyst charge in the catalyst tube, is a homogenized mixture of only one type $S^i$ of the aforementioned annular unsupported catalysts and only one type $S^i$ of annular shaped inert bodies (both shaped body types preferably have the same ring geometry), the proportion by weight of the shaped diluent bodies (the bulk densities of shaped catalyst bodies and shaped diluent bodies generally differ only slightly) being normally from 5 to 40% by weight, or from 10 to 40% by weight, or from 20 to 40% by weight, or from 25 to 35% by weight. Downstream of this first charge section is then advantageously disposed, up to the end of the length of the catalyst charge (i.e., for example, for a length of from 1.00 to 3.00 m or from 1.00 to 2.70 m, preferably from 1.40 to 3.00 m or from 2.00 to 3.00 m), either a bed of the only one type $S^i$ of annular unsupported catalysts diluted only to a lesser extent (than in the first section) with the only one type $S^i$ of annular shaped inert bodies, or, most preferably, an exclusive (undiluted) bed of the same only one type $S^i$ of annular unsupported catalyst. Of course, it is also possible to select a uniform dilution over the entire catalyst tube length. The fixed catalyst bed will be configured in a corresponding manner when the geometries are spherical.

Otherwise, the heterogeneously catalyzed partial gas phase oxidation of propylene to acrolein or of isobutene to methacrolein can be performed in a tube bundle reactor having one or more temperature zones, as described in the prior art (cf., for example, WO 2005/03093, DE-A 10 2007 005 602 and DE-A 10 2004 025 445, and the prior art cited in these documents).

Useful active compositions for the geometric shaped catalyst bodies of an inventive catalyst tube charge also include multielement oxides of the general formula II

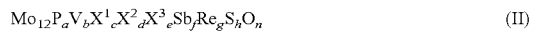

$$Mo_{12}P_aV_bX^1_cX^2_dX^3_eSb_fRe_gS_hO_n \quad \text{(II)}$$

where
  $X^1$=potassium, rubidium and/or cesium,
  $X^2$=copper and/or silver,
  $X^3$=cerium, boron, zirconium, manganese and/or bismuth,
  a=0.5 to 3,
  b=0.01 to 3,
  c=0.2 to 3,
  d=0.01 to 2,
  e=0 to 2,
  f=0.01 to 2,
  g=0 to 1,
  h=0.001 to 0.5, and
  n=a number which is determined by the valency and frequency of the elements in II other than oxygen.

Such geometric shaped catalyst bodies are suitable advantageously especially for a heterogeneously catalyzed partial gas phase oxidation of methacrolein to methacrylic acid.

Aforementioned shaped catalyst bodies are preferably likewise annular unsupported catalysts, as obtainable, for example, by the procedure described in EP-A 467 144. Useful median ring geometries are in particular the individual geometries recommended in EP-A 467 144 and those recommended with regard to the multielement oxides I in this document. A preferred median ring geometry is that where E×L× I=7 mm×7 mm×3 mm (cf. also DE-A 10 2007 005 602).

A structured dilution with annular shaped inert bodies can be effected, for example, as described for the case of the heterogeneously catalyzed partial oxidation of propylene to acrolein. Otherwise, the partial oxidation process conditions described in EP-A 467 144 and DE-A 10 2007 005 602 may be employed. For the heterogeneously catalyzed partial gas phase oxidation of hydrocarbons having at least four carbon atoms (especially n-butane, n-butenes and/or benzene) to maleic anhydride, useful multielement oxide active compositions for geometric shaped catalyst bodies to be used in accordance with the invention are advantageously those of the general formula II,

$$V_1P_bFe_cX^1_dX^2_eO_n \quad \text{(III)}$$

in which the variables are each defined as follows:
$X^1$=Mo, Bi, Co, Ni, Si, Zn, Hf, Zr, Ti, Cr, Mn, Cu, B, Sn and/or Nb,
$X^2$=K, Na, Rb, Cs and/or Tl,
b=0.9 to 1.5,
c=0 to 0.1,
d=0 to 0.1,
e=0 to 0.1, and
n=a number which is determined by the valency and frequency of the elements in III other than oxygen.

Advantageously, these shaped catalyst bodies are likewise annular unsupported catalysts, as obtainable, for example, according to WO 03/078310, WO 01/68245, DE-A 10 2005 035 978 and DE-A 10 2007 005 602. Useful median ring geometries are in particular the individual geometries recommended in the aforementioned documents and the individual geometries recommended with regard to the multielement oxides I in this document. A preferred median ring geometry is that where E×L×I=5 mm×3.2 mm×2.5 mm (see also DE-A 10 2007 005 602).

A structured dilution with annular shaped inert bodies can be effected, for example, as described for the case of the heterogeneously catalyzed partial oxidation of propylene to acrolein.

Otherwise, the partial oxidation process conditions recommended in WO 03/078 310, WO 01/68245, DE-A 10 2005 035 978 and DE-A 10 2007 005 602 can be applied.

For the heterogeneously catalyzed partial gas phase oxidation of acrolein to acrylic acid, useful multielement oxide active compositions for geometric shaped catalyst bodies to be used in accordance with the invention are advantageously those of the general formula IV $$Mo_{12}V_a X^1_b X^2_c X^3_d X^4_e X^5_f X^6_g O_n \quad (IV)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40, and
n=a number which is determined by the valency and frequency of the elements in IV other than oxygen.

Advantageously, these shaped catalyst bodies are annular or spherical coated catalysts, as obtainable, for example, according to DE-A 10 2004 025 445, DE-A 10 350 822, DE-A 10 2007 010 422, US 2006/0205978 and EP-A 714 700, and the prior art cited in these documents.

Useful median ring geometries or median sphere geometries are in particular the individual geometries recommended in the aforementioned documents. A preferred median ring geometry is that where E×L×I=7 mm×3 mm×4 mm for the parent annular shaped support bodies.

The active composition coating thickness may be from 10 to 1000 μm, preferably from 50 to 500 μm and more preferably from 150 to 250 μm. Favorable coating thicknesses are those of the exemplary embodiments of EP-A 714 700.

For a heterogeneously catalyzed partial gas phase oxidation of acrolein to acrylic acid, the catalyst charge in the catalyst tube is preferably either configured uniformly with only one inventive type $S^i$ of coated catalyst rings over the entire length of the catalyst tube or structured as follows.

Positioned at the catalyst tube inlet (in flow direction of the reaction gas mixture), for a length of from 10 to 60%, preferably from 10 to 50%, more preferably from 20 to 40% and most preferably from 5 to 35% (i.e., for example, for a length of from 0.70 to 1.50 m, preferably from 0.90 to 1.20 m), in each case of the total length of the catalytically active catalyst charge in the catalyst tube, is a homogenized mixture composed of only one type $S^i$ of the abovementioned annular coated catalysts and only one type $S^i$ of annular shaped inert bodies (both shaped body types preferably have the same ring geometry), the proportion by weight of the shaped diluent bodies (the bulk densities of shaped catalyst bodies and of shaped diluent bodies generally differ only slightly) being normally from 5 to 40% by weight, or from 10 to 40% by weight, or from 20 to 40% by weight, or from 25 to 35% by weight. Downstream of this first charge section is then advantageously disposed, up to the end of the length of the catalyst charge (i.e., for example, for a length of from 2.00 to 3.00 m, preferably from 2.50 to 3.00 m), either a bed of the only one type $S^i$ of annular unsupported catalysts diluted only to a lesser extent (than in the first section) with the only one type $S^i$ of annular shaped inert bodies, or, most preferably, an exclusive (undiluted) bed of the same only one type $S^i$ of annular coated catalyst. The fixed catalyst bed will be configured in a corresponding manner when the coated catalyst geometry is spherical.

Otherwise, the heterogeneously catalyzed gas phase oxidation of acrolein to acrylic acid can be performed in a tube bundle reactor having one or more temperature zones as described in the prior art (cf., for example, DE-A 10 2004 025 445, DE-A 10 350 822, DE-A 10 2007 010 422, US 2006/0205978 and EP-A 714 700, and the prior art cited in these documents).

A multielement oxide comprising V and Sb (especially one according to the documents U.S. Pat. No. 6,528,683, or U.S. Pat. No. 6,586,361, or U.S. Pat. No. 6,362,345) is suitable especially for a heterogeneously catalyzed partial oxidation of o-xylene and/or naphthalene to phthalic anhydride.

In this case, preference is given to using the aforementioned multielement oxides as annular or as spherical coated catalysts. Useful support bodies are in particular those which consist to an extent of at least 80% by weight of titanium dioxide. Exemplary median ring geometries include the ring geometries E×L×I=8 mm×6 mm×5 mm, or 8 mm×6 mm×4 mm, or 8 mm×6 mm×3 mm and 7 mm×7 mm×4 mm.

Shaped catalyst bodies whose active composition comprises elemental silver on an oxidic support body are suitable (in particular as supported catalysts) especially for a heterogeneously catalyzed partial gas phase oxidation of ethylene to ethylene oxide (cf. EP-A 496470).

In this case, the shaped catalyst body geometry may likewise be spherical or annular. Useful shaped support bodies are in particular those which consist to an extent of at least 80% by weight of aluminum oxide (e.g. $Al_2O_3$).

Exemplary median sphere geometries here include the sphere diameters 4 mm, 5 mm and 7 mm.

Quite generally, in the processes described for heterogeneously catalyzed partial gas phase oxidation, a pure shaped inert body bed whose length, based on the total length of the fixed catalyst bed, within the catalyst tube is appropriately from 1 or 5 to 20% can introduce the fixed catalyst bed in flow direction of the reaction gas. It is normally utilized as a heating zone for the reaction gas mixture.

Generally, it is advantageous in the process according to the invention when the median $D_S^i$ of the longest dimension $L_S^i$ of one type $S^i$ used in the catalyst tube to charge a fixed catalyst bed section has the following ratio relative to the internal diameter R of the catalyst tube: $R/D_S^i$ from 1.5 to 5, preferably from 2 to 4 and more preferably from 3 to 3.5.

Moreover, it is advantageous for the process according to the invention when the arithmetic mean $M_S^i$ of the longest dimensions $L_S^i$ which form the basis of the median $D_S^i$ deviates from $D_S^i$ by not more than 10%, preferably not more than 5% (with $D_S^i$ as the reference basis). All statements in this document apply especially when the geometric shaped catalyst bodies and the geometric shaped inert bodies are rings. The catalyst tubes can otherwise generally be filled as described in WO 2006/094 766 and WO 2005/113 123 and JP-A 2004 195 279.

All statements made in this document also apply especially to the coated catalysts having a multielement oxide active composition comprising Mo and V from documents EP-A 1 254 707, EP-A 1 254 710, EP-A 1 254 709, WO 2004/035528, DE-A 102 48 584, DE-A 102 54 278, DE-A 102 54 279, WO 02/06199 and WO 02/051539, and to the partial oxidations, catalyzed by these coated catalysts, of propane to acrolein and/or acrylic acid, and of isobutane to methacrolein and/or methacrylic acid.

In addition, all statements made in this document also apply especially to the coated catalysts having a multielement oxide active composition comprising Mo and V from DE-A 10 2007 010 422, and to the partial oxidations catalyzed by these coated catalysts (especially of acrolein to acrylic acid).

The present invention thus comprises especially the following embodiments:

1. A process for charging a longitudinal section of a catalyst tube with a uniform fixed catalyst bed section whose active composition is at least one multielement oxide which comprises
   a) the elements Mo, Fe and Bi, or
   b) the elements Mo and V, or
   c) the element V and additionally P and/or Sb,
   or whose active composition comprises elemental silver on an oxidic support body, and which consists of a single type $S^i$ or of a homogenized mixture of a plurality of mutually distinguishable types $S^i$ of geometric shaped catalyst bodies or of geometric shaped catalyst bodies and geometric shaped inert bodies, where the median of the longest dimensions $L_S^i$ of the geometric shaped bodies of one type $S^i$ has a value $D_S^i$, wherein, at least within one type $S^i$ of geometric shaped bodies, the proviso M that
   from 40 to 70% of the total number of geometric shaped bodies belonging to $S^i$ has a longest dimension $L_S^i$ for which $0.98 \cdot D_S^i \leq L_S^i \leq 1.02 \cdot D_S^i$, at least 10% of the total number of the geometric shaped bodies belonging to $S^i$ has a longest dimension $L_S^i$ for which $0.94 \cdot D_S^i \leq L_S^i < 0.98 \cdot D_S^i$, at least 10% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot d_S^i > L_S^i$, and less than 5% of the total number of the geometric shaped bodies belonging to $S^i$ has a longest dimension $L_S^i$ for which $1.10 \cdot D_S^i < L_S^i$ is satisfied.

2. A process according to embodiment 1, wherein, at least within one type $S^i$ of geometric shaped bodies, the proviso M* that
   from 50 to 60% of the total number of geometric shaped bodies belonging to $S^i$ has a longest dimension $L_S^i$ for which $0.98 \cdot D_S^i \leq L_S^i \leq 1.02 \cdot D_S^i$, at least 15% of the total number of the geometric shaped bodies belonging to $S^i$ has a longest dimension $L_S^i$ for which $0.94 \cdot D_S^i \leq L_S^i < 0.98 \cdot D_S^i$, at least 15% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot D_S^i > L_S^i$, and less than 5% of the total number of the geometric shaped bodies belonging to $S^i$ has the longest dimension $L_S^i$ for which $1.10 \cdot D_S^i < L_S^i$ is satisfied.

3. A process according to embodiment 1, wherein, at least within one type $S^i$ of geometric shaped bodies, the proviso M** that
   from 50 to 60% of the total number of geometric shaped bodies belonging to $S^i$ has a longest dimension $L_S^i$ for which $0.98 \cdot D_S^i \leq L_S^i \leq 1.02 \cdot D_S^i$, at least 20% of the total number of the geometric shaped bodies belonging to $S^i$ has a longest dimension $L_S^i$ for which $0.94 \cdot D_S^i \leq L_S^i < 0.98 \cdot D_S^i$, at least 20% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot D_S^i > L_S^i$, and less than 5% of the total number of the geometric shaped bodies belonging to $S^i$ has a longest dimension $L_S^i$ for which $1.10 \cdot D_S^i < L_S^i$ is satisfied.

4. A process according to any of embodiments 1 to 3, wherein the fixed catalyst bed section consists of only a single type $S^i$ of annular or of spherical shaped catalyst bodies.

5. A process according to embodiment 1, wherein the shaped catalyst bed section consists of a homogenized mixture of only one type of annular shaped catalyst bodies and only one type of annular shaped inert bodies, wherein both the only one type of annular shaped catalyst bodies and the only one type of annular shaped inert bodies satisfy the proviso M.
6. A process according to embodiment 2, wherein the shaped catalyst bed section consists of a homogenized mixture of only one type of annular shaped catalyst bodies and only one type of annular shaped inert bodies, wherein both the only one type of annular shaped catalyst bodies and the only one type of annular shaped inert bodies satisfy the proviso M*.
7. A process according to embodiment 3, wherein the shaped catalyst bed section consists of a homogenized mixture of only one type of annular shaped catalyst bodies and only one type of annular shaped inert bodies, wherein both the only one type of annular shaped catalyst bodies and the only one type of annular shaped inert bodies satisfy the proviso M**.
8. A process for charging a catalyst tube with a fixed catalyst bed which consists of a plurality of successive and mutually different catalytically active fixed catalyst bed sections, each of which is intrinsically homogeneous, and where the active composition of all fixed catalyst bed sections comprises at least one multielement oxide which comprises
   a) the elements Mo, Fe and Bi, or
   b) the elements Mo and V, or
   c) the element V and additionally P and/or Sb,
   or whose active composition comprises elemental silver on an oxidic support body, and the individual fixed catalyst bed section consists of a single type $S^i$ or of a homogenized mixture of a plurality of mutually distinguishable types $S^i$ of geometric shaped catalyst bodies and geometric shaped inert bodies, wherein, in each individual fixed catalyst bed section, all types $S^i$ of geometric shaped bodies present therein in each case satisfy the proviso M according to embodiment 1, or the proviso M* according to embodiment 2, or the proviso M** according to embodiment 3.
9. A process according to embodiment 8, wherein all geometric shaped bodies are rings or spheres.
10. A process according to embodiment 9, wherein all geometric shaped bodies have the same ring geometry or the same sphere geometry.
11. A process according to embodiment 10, wherein the combined medium $D^{inert}_{cat}$, formed over the total number G of all longest dimensions $L_{cat}$ of the geometric shaped catalyst bodies and all longest dimensions $L_{inert}$ of the geometric shaped inert bodies, and the longest dimensions $L_{inert}$ and $L_{cat}$ (i.e. $L_{cat,inert}$) satisfy the proviso $M^{G*}$ that
from 40 to 70% of the total number G has a longest dimension $L_{cat,inert}$ for which $$0.98 \cdot D^{inert}_{cat} \leq L_{cat,inert} \leq 1.02 \cdot D^{inert}_{cat},$$

at least 10% of the total number G has a longest dimension $L_{cat,inert}$ for which $$0.94 \cdot D^{inert}_{cat} \leq L_{cat,inert} < 0.98 \cdot D^{inert}_{cat},$$

at least 10% of the total number G has a longest dimension $L_{cat,inert}$ for which $$1.02 \cdot D^{inert}_{cat} < L_{cat,inert} \leq 1.10 \cdot D^{inert}_{cat},$$

less than 5% of the total number G has a longest dimension $L_{cat,inert}$ for which $$0.94 \cdot D^{inert}_{cat} > L_{cat,inert}, \text{ and}$$

less than 5% of the total number G has a longest dimension $L_{cat,inert}$ for which $$1.10 \cdot D^{inert}_{cat} < L_{cat,inert}$$

is satisfied.
12. A process according to embodiment 11, wherein the entire fixed catalyst bed comprises only one type of annular shaped catalyst bodies and only one type of annular shaped inert bodies or only one type of spherical shaped catalyst bodies and only one type of spherical shaped inert bodies.
13. A process according to any of embodiments 5 to 7, wherein the shaped catalyst bodies and the shaped inert bodies are not annular but spherical.
14. A tube bundle reactor comprising at least one catalyst tube which has been charged by a process according to any of embodiments 1 to 13.
15. A process for heterogeneously catalyzed partial gas phase oxidation of an organic compound in a tube bundle reactor, wherein the tube bundle reactor is a tube bundle reactor according to embodiment 14.
16. A process according to embodiment 15, wherein the heterogeneously catalyzed partial gas phase oxidation is that of propylene to acrolein and/or that of acrolein to acrylic acid.
17. A process for preparing organic compounds (e.g. all of those mentioned in this document, for example acrolein, acrylic acid, methacrylic acid, maleic anhydride, ethylene oxide and phthalic anhydride), which comprises a process according to any of embodiments 1 to 12.

Otherwise, all data in this document, unless explicitly stated otherwise, are based on a temperature of 25° C. and a pressure of 1 atm.

EXAMPLE AND COMPARATIVE EXAMPLES

Comparative Example 1

Like the unsupported catalyst BVK 3 in WO 2005/030 393, using TIMREX T 44 from Timcal AG (Bodio, Switzerland) as auxiliary graphite, one type of annular unsupported catalysts of stoichiometry (without taking account of graphite still present)

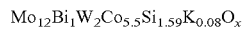

was prepared.

The median geometry of the annular unsupported catalysts was E×L×I=5 mm×3 mm×2 mm.

Between the median of its longest dimension $D_S^i$ (5.83 mm) and the individual longest dimensions $L_S^i$, the following condition was satisfied:

$$0.99 \cdot 5.83 \text{ mm} \leq L_S^i \leq 1.01 \cdot 5.83 \text{ mm}.$$

A catalyst tube (V2A steel; external diameter 21 mm, wall thickness 3 mm, internal diameter 15 mm, length 100 cm) was charged using steatite shaped inert body rings of the same annular median geometry in flow direction of the later reaction gas as follows:
Section 1: length 30 cm, bed only of the inert shaped body rings;
Section 2: length 70 cm, bed only of the annular unsupported catalysts.

The catalyst tube was heated by means of a nitrogen-sparged salt bath.

The catalyst tube was charged with a charge gas mixture (mixture of air, polymer-grade propylene and nitrogen) of the following composition:

5% by volume of propylene,
10% by volume of molecular oxygen, and
as the remainder to 100% by volume, $N_2$.

The propylene loading of the fixed catalyst bed was selected at 50 l (STP)/(l·h). The salt bath temperature was adjusted such that the propylene conversion, based on a single pass of the reaction gas mixture through the catalyst tube, was 95 mol %.

The selectivity of the resulting product of value formation of acrolein and acrylic acid was 95.7 mol %.

Comparative Example 2

The procedure was as in Comparative example 1. To charge section 2 of the catalyst tube, however, a homogenized mixture of annular unsupported catalysts of the same median geometry and active composition was used, except that the following relationships were satisfied between the median of the longest dimensions and the individual longest dimensions:

For 80% of the rings: $0.98 \cdot 5.83$ mm $\leq L_S^i \leq 1.02 \cdot 5.83$ mm.
For 20% of the rings: $1.02 \cdot 5.83$ mm $< L_S^i \leq 1.10 \cdot 5.83$ mm.

The selectivity of the resulting product of value formation of acrolein and acrylic acid was, under otherwise identical operating conditions, 95.8 mol %.

Example

The procedure was as in Comparative example 1. To charge section 2 of the catalyst tube, however, a homogenized mixture of annular unsupported catalysts of the same median geometry and active composition was used, except that the following relationships were satisfied between the median of the longest dimensions and the individual longest dimensions:

For 60% of the rings: $0.98 \cdot 5.73$ mm $\leq L_S^i \leq 1.02 \cdot 5.73$ mm.
For 20% of the rings: $0.94 \cdot 5.73$ mm $\leq L_S^i < 0.98 \cdot 5.73$ mm.
For 20% of the rings: $1.02 \cdot 5.73$ mm $< L_S^i \leq 1.10 \cdot 5.73$ mm.

The selectivity of the resulting product of value formation of acrolein and acrylic acid was, under otherwise identical operating conditions, 96.2 mol %.

U.S. Provisional Patent Application No. 60/910,908, filed Apr. 10, 2007, is incorporated into the present patent application by literature reference. With regard to the abovementioned teachings, numerous changes and deviations from the present invention are possible.

It can therefore be assumed that the invention, within the scope of the appended claims, can be performed differently from the way described specifically herein.

The invention claimed is:

1. A tube bundle reactor comprising at least one catalyst tube which has been charged by a process for charging a longitudinal section of a catalyst tube with a uniform fixed catalyst bed section whose active composition is at least one multielement oxide which comprises
   a) the elements Mo, Fe and Bi, or
   b) the elements Mo and V, or
   c) the element V and additionally P and/or Sb,
   on an oxidic support body, and
   wherein the uniform fixed catalyst bed section consists of a single type $S^i$ or of a homogenized mixture of a plurality of mutually distinguishable types $S^i$ of geometric shaped catalyst bodies or of geometric shaped catalyst bodies and geometric shaped inert bodies, where the median of the longest dimensions $L_S^i$ of the geometric shaped bodies of one type $S^i$ has a value $D_S^i$, wherein, at least within one type $S^i$ of geometric shaped bodies, the proviso M that
   from 40 to 70% of the total number of geometric shaped bodies belonging to $S^i$ has a longest dimension $L_S^i$ for which $0.98 \cdot D_S^i \leq L_S^i \leq 1.02 \cdot D_S^i$, at least 10% of the total number of the geometric shaped bodies belonging to $S^i$ has a longest dimension $L_S^i$ for which $0.94 \cdot D_S^i \leq L_S^i < 0.98 \cdot D_S^i$, at least 10% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot D_S^i > L_S^i$, and less than 5% of the total number of the geometric shaped bodies belonging to $S^i$ has a longest dimension $L_S^i$ for which $1.10 \cdot D_S^i < L_S^i$ is satisfied.

2. The tube bundle reactor according to claim 1, wherein, at least within one type $S^i$ of geometric shaped bodies, satisfies the proviso M* that
   from 50 to 60% of the total number of geometric shaped bodies belonging to $S^i$ has a longest dimension $L_S^i$ for which $0.98 \cdot D_S^i \leq L_S^i \leq 1.02 \cdot D_S^i$, at least 15% of the total number of the geometric shaped bodies belonging to $S^i$ has a longest dimension $L_S^i$ for which $0.94 \cdot D_S^i \leq L_S^i < 0.98 \cdot D_S^i$, at least 15% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension L for which $0.94 \cdot D_S^i > L_S^i$, and less than 5% of the total number of the geometric shaped bodies belonging to $S^i$ has a longest dimension $L_S^i$ for which $1.10 \cdot D_S^i < L_S^i$.

3. The tube bundle reactor according to claim 2, wherein the uniform fixed catalyst bed section consists of a homogenized mixture of only one type of annular shaped catalyst bodies and only of one type of annular shaped inert bodies, wherein both the only one type of annular shaped catalyst bodies and the only one type of annular shaped inert bodies satisfy the proviso M*.

4. The tube bundle reactor according to claim 1, wherein, at least within one type $S^i$ of geometric shaped bodies, satisfies the proviso M** that from 50 to 60% of the total number of geometric shaped bodies belonging to $S^i$ has a longest dimension $L_S^i$ for which $0.98 \cdot D_S^i \leq L_S^i \leq 1.02 \cdot D_S^i$, at least 20% of the total number of the geometric shaped bodies belonging to $S^i$ has a longest dimension $L_S^i$ for which $0.94 \cdot D_S^i \leq L_S^i < 0.98 \cdot D_S^i$, at least 20% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot D_S^i > L_S^i$, and less than 5% of the total number of the geometric shaped bodies belonging to $S^i$ has a longest dimension L for which $1.10 \cdot D_S^i < L_S^i$.

5. The tube bundle reactor according to claim 1, wherein the fixed catalyst bed section consists of only a single type $S^i$ of annular or of spherical shaped catalyst bodies.

6. The tube bundle reactor according to claim 1, wherein the uniform fixed catalyst bed section consists of a homogenized mixture of only one type of annular shaped catalyst bodies and only of one type of annular shaped inert bodies, wherein both the only one type of annular shaped catalyst bodies and the only one type of annular shaped inert bodies satisfy the proviso M.

7. The tube bundle reactor according to claim 1, wherein all geometric shaped bodies are rings or spheres.

8. The tube bundle reactor according to claim 7, wherein all geometric shaped bodies have the same ring geometry or the same sphere geometry.

9. The tube bundle reactor according to claim 8, wherein a combined medium $D^{inert}_{cat}$, formed over a total number G of all longest dimensions $L_{cat}$ of the geometric shaped catalyst bodies and all longest dimensions $L_{inert}$ of the geometric shaped inert bodies, and the longest dimensions $L_{inert}$ and $L_{cat}$ represented by $L_{cat,inert}$ satisfy the proviso $M^{G^*}$ that from 40 to 70% of the total number G has a longest dimension $L_{cat,inert}$ for which $0.98 \cdot D^{inert}_{cat} \leq L_{cat,inert} \leq 1.02 \cdot D^{inert}_{cat}$, at least 10% of the total number G has a longest dimension $L_{cat,inert}$ for which $0.94 \cdot D^{inert}_{cat} \leq L_{cat,inert} < 0.98 \cdot D^{inert}_{cat}$, at least 10% of the total number G has a longest dimension $L_{cat,inert}$ for which $1.02 \cdot D^{inert}_{cat} < L_{cat,inert} \leq 1.10 \cdot D^{inert}_{cat}$, less than 5% of the total number G has a longest dimension $L_{cat,inert}$ for which $0.94 \cdot D^{inert}_{cat} > L_{cat,inert}$, and less than 5% of the total number G has a longest dimension $L_{cat,inert}$ for which $1.10 \cdot D^{inert}_{cat} < L_{cat,inert}$.

10. The tube bundle reactor according to claim 8, wherein the entire fixed catalyst bed comprises only one type of annular shaped catalyst bodies and only one type of annular shaped inert bodies or only one type of spherical shaped catalyst bodies and only one type of spherical shaped inert bodies.

11. The tube bundle reactor according to claim 1, wherein the shaped catalyst bodies and the shaped inert bodies are not annular but spherical.

12. The tube bundle reactor according to claim 1, wherein the uniform fixed catalyst bed section does not comprises silver.

13. A process for heterogeneously catalyzed partial gas phase oxidation of an organic compound in a tube bundle reactor, comprising:
    at least partially oxidizing the organic compound in the gas phase in the tube bundle reactor according to claim 1.

14. The process according to claim 13, wherein the organic compound is propylene and the oxidizing includes at least one of oxidizing the propylene to form acrolein and oxidizing acrolein to form acrylic acid.

15. A tube bundle reactor comprising at least one catalyst tube which has been charged by a process for charging a catalyst tube with a fixed catalyst bed which consists of a plurality of successive and mutually different catalytically active fixed catalyst bed sections, each of which is intrinsically homogeneous, and where the active composition of all fixed catalyst bed sections comprises at least one multielement oxide which comprises
    a) the elements Mo, Fe and Bi, or
    b) the elements Mo and V, or
    c) the element V and additionally P and/or Sb,
    on an oxidic support body, and
    wherein the individual fixed catalyst bed section consists of a single type $S^i$ or of a homogenized mixture of a plurality of mutually distinguishable types $S^i$ of geometric shaped catalyst bodies and geometric shaped inert bodies, wherein, in each individual fixed catalyst bed section, all types $S^i$ of geometric shaped bodies present therein in each case satisfy the proviso M that
    from 40 to 70% of the total number of geometric shaped bodies belonging to $S^i$ has a longest dimension $L_S^i$ for which $0.98 \cdot D_S^i \leq L_S^i \leq 1.02 \cdot D_S^i$, at least 10% of the total number of the geometric shaped bodies belonging to $S^i$ has a longest dimension $L_S^i$ for which $0.94 \cdot D_S^i \leq L_S^i < 0.98 \cdot D_S^i$, at least 10% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot D_S^i > L_S^i$, and less than 5% of the total number of the geometric shaped bodies belonging to $S^i$ has a longest dimension $L_S^i$ for which $1.10 \cdot D_S^i < L_S^i$.

16. The tube bundle reactor according to claim 15, wherein the fixed catalyst bed sections do not comprise silver.

17. A tube bundle reactor, comprising:

at least one catalyst tube comprising a uniform fixed catalyst bed section containing at least one multielement oxide which comprises a) the elements Mo, Fe and Bi, or b) the elements Mo and V, or c) the element V and additionally P and/or Sb, on an oxidic support body, and which consists of a single type $S^i$ or of a homogenized mixture of a plurality of mutually distinguishable types $S^i$ of geometric shaped catalyst bodies or of geometric shaped catalyst bodies and geometric shaped inert bodies, where the median of the longest dimensions $L_S^i$ of the geometric shaped bodies of one type $S^i$ has a value $D_S^i$, wherein, at least within one type $S^i$ of geometric shaped bodies, the proviso M that from 40 to 70% of the total number of geometric shaped bodies belonging to $S^i$ has a longest dimension $L_S^i$ for which $0.98 \cdot D_S^i \leq L_S^i \leq 1.02 \cdot D_S^i$, at least 10% of the total number of the geometric shaped bodies belonging to $S^i$ has a longest dimension $L_S^i$ for which $0.94 \cdot D_S^i \leq L_S^i < 0.98 \cdot D_S^i$, at least 10% of the total number of the geometric shaped bodies belonging to $S^i$ has a longest dimension $L_S^i$ for which $1.02 \cdot D_S^i < L_S^i \leq 1.10 \cdot D_S^i$, less than 5% of the total number of geometric shaped bodies belonging to $S^i$ has a longest dimension $L_S^i$ for which $0.94 \cdot D_S^i > L_S^i$, and less than 5% of the total number of geometric shaped bodies belonging to $S^i$ has a longest dimension $L_S^i$ for which $1.10 \cdot D_S^i < L_S^i$ is satisfied.

18. The tube bundle reactor according to claim 17, wherein the uniform fixed catalyst bed section does not comprise silver.

* * * * *